United States Patent
Goulden

(10) Patent No.: US 7,288,413 B2
(45) Date of Patent: Oct. 30, 2007

(54) COMBINED CHEMICAL AND IMMUNOCHEMICAL FECAL OCCULT BLOOD TEST

(75) Inventor: Leslie Goulden, Los Altos, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 11/203,050

(22) Filed: Aug. 12, 2005

(65) Prior Publication Data

US 2007/0037296 A1    Feb. 15, 2007

(51) Int. Cl.
| | |
|---|---|
| G01N 15/06 | (2006.01) |
| G01N 21/00 | (2006.01) |
| G01N 21/03 | (2006.01) |
| G01N 21/77 | (2006.01) |
| G01N 31/22 | (2006.01) |
| G01N 33/53 | (2006.01) |
| G01N 33/72 | (2006.01) |
| G01N 33/558 | (2006.01) |
| G01N 33/566 | (2006.01) |
| C12Q 1/00 | (2006.01) |
| C12M 1/34 | (2006.01) |
| C12M 3/00 | (2006.01) |

(52) U.S. Cl. .................. 436/66; 436/165; 436/169; 436/501; 436/514; 436/807; 422/55; 422/56; 422/58; 422/61; 422/68.1; 435/4; 435/7.1; 435/287.1; 435/287.2; 435/287.9; 435/288.7

(58) Field of Classification Search .......... 436/501, 436/514, 66, 807, 165, 169; 422/55, 56, 422/58, 61, 68.1; 435/4, 7.1, 287.1, 287.2, 435/287.9, 288.7
See application file for complete search history.

(56) References Cited

U.S. PATENT DOCUMENTS

| 4,427,769 A | * | 1/1984 | Adlercreutz et al. ....... 435/7.92 |
| 4,717,656 A | | 1/1988 | Swanljung ..................... 435/7 |
| 4,789,629 A | | 12/1988 | Baker et al. .................... 435/7 |
| 5,100,619 A | | 3/1992 | Baker et al. ................... 422/58 |
| 5,182,191 A | * | 1/1993 | Fan et al. ..................... 435/7.9 |
| 5,747,344 A | | 5/1998 | Cleator ....................... 436/66 |
| 5,948,687 A | | 9/1999 | Cleator ....................... 436/66 |
| 6,017,767 A | * | 1/2000 | Chandler .................... 436/514 |
| 6,326,214 B1 | | 12/2001 | Liu et al. ..................... 436/518 |
| 6,410,336 B1 | * | 6/2002 | Augurt ........................ 436/66 |
| 6,436,714 B1 | * | 8/2002 | Clawson et al. .............. 436/66 |
| 2004/0194206 A1 | | 10/2004 | Kieturakis et al. ............. 4/661 |

OTHER PUBLICATIONS

Imafuku Y., Nagai T., Yoshida H., *The effect of toilet sanitizers and detergents on immunological occult blood tests*, Clin. Chim. Acta. Sep. 30, 1996; 253(1-2): 51-9, abstract only.

(Continued)

*Primary Examiner*—Long V. Le
*Assistant Examiner*—Jacqueline A. DiRamio
(74) *Attorney, Agent, or Firm*—Michael Fedrick; Sheldon Mak; Rose & Anderson

(57) ABSTRACT

Methods for testing a fecal sample for the presence of hemoglobin, comprising performing a chemical fecal occult blood test on the sample and then performing an immunochemical fecal occult blood test on a portion of the sample exposed to the chemical reagents used in the chemical fecal occult blood test.

14 Claims, 7 Drawing Sheets

OTHER PUBLICATIONS

Chunli Xu; Zhujun Zhang, *Fluorescence Determination of Hydrogen Peroxide Using Hemoglobin as a Mimetic Enzyme of Peroxidase*, Analytical Sciences Dec. 2001, vol. 17, pp. 1449-1451.

Hisahiko Iwamoto; Yoshihiro Motomiya; Keisuke Miura; Masayo Morisawa; Yoshimichi Yoshimura; Ikuro Maruyama, *Immunochemical Assay of Hemoglobin with Nε- (Carboxymethyl) lysine at Lysine 66 of the B Chain*, Clinical Chemistry 47:7 1249-1255 (2001).

Seracult Test For Fecal Occult Blood; Texas Tech Medical Center. Hemo FEC Detailed information.

Yuji Imafuku, Toshihiko Nagai, Hiroshi Yoshida, "The effect of toilet sanitizers and detergents on immunological occult blood tests," Clinica Chimica Acta, 253:51-59 (1996).

Martin Fleisher and Ronald J. Schoengold, "Occult Blood," in Point-of-Care Testing, Performance Improvement and Evidence-Based Outcomes, edited by James H. Nichols, pp. 325-351 (2002).

\* cited by examiner

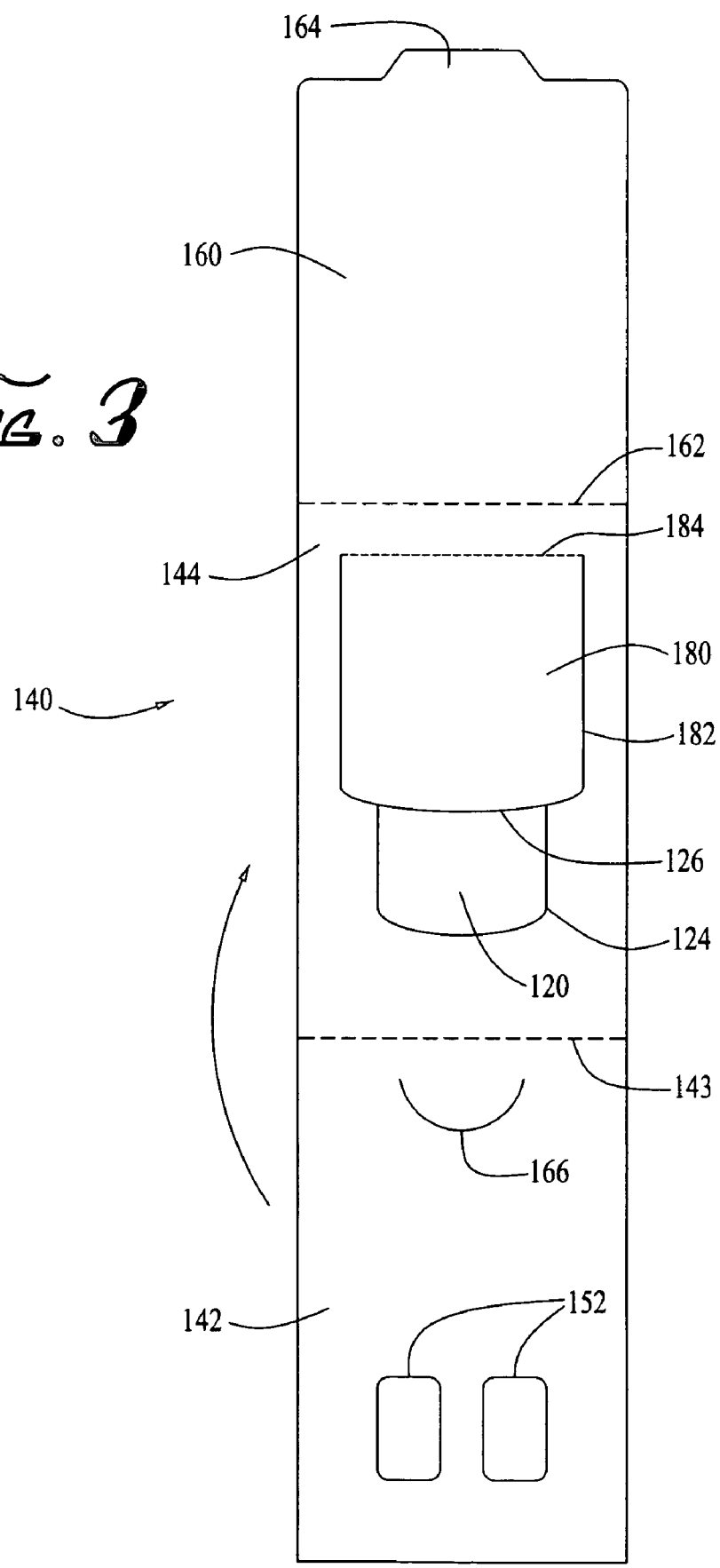

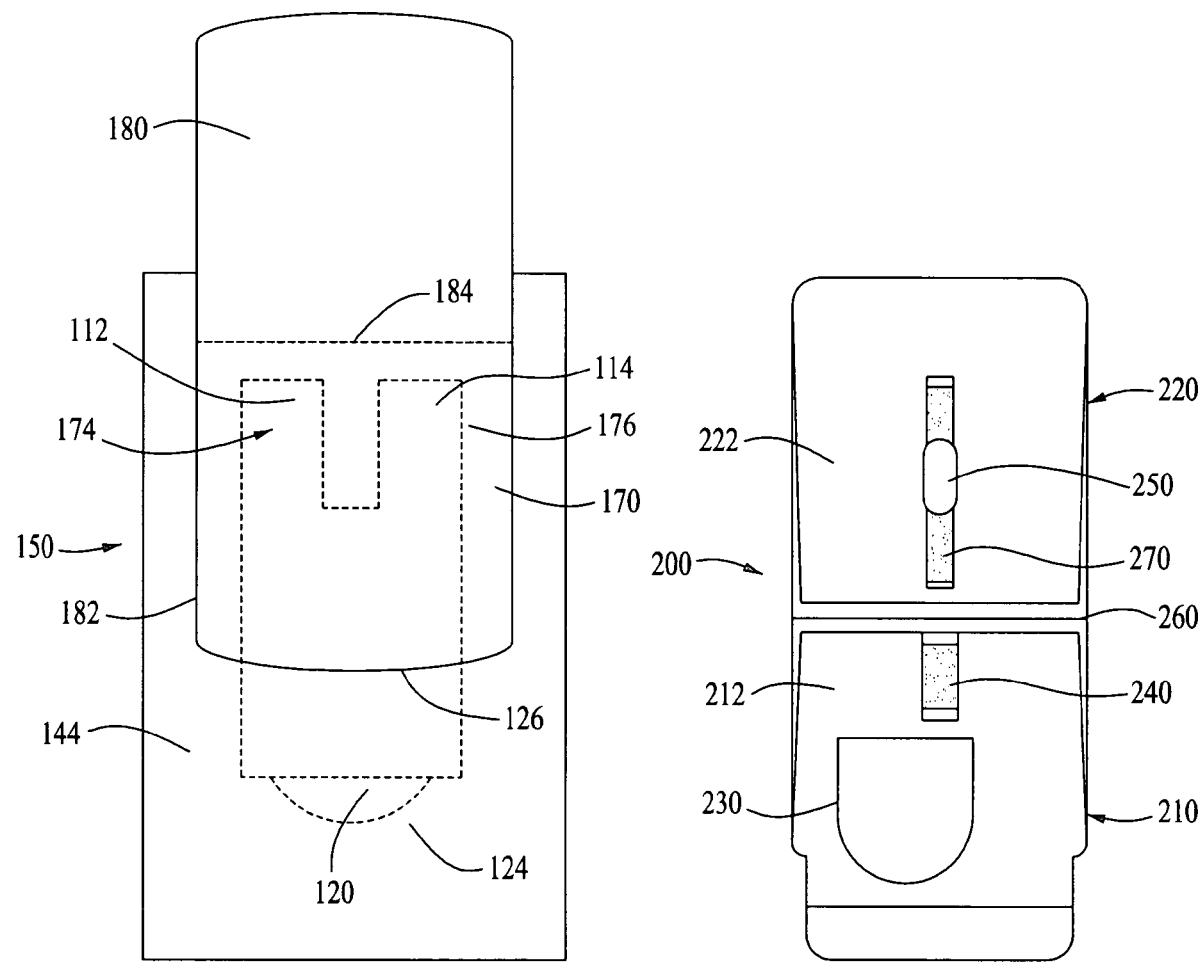

COMBINED CHEMICAL AND IMMUNOCHEMICAL FECAL OCCULT BLOOD TEST

BACKGROUND

Colorectal cancer is a leading cause of cancer-related deaths worldwide, and is the second leading cause of cancer-related deaths in the United States. Although a patient's prognosis is good if the cancer is caught early, when the site of the cancer is confined to its site of origin, cure rates fall once the cancer has spread. Screening measures such as sigmoidoscopy and colonoscopy have demonstrated a high rate of early detection of colorectal cancer, but are expensive and can cause a great deal of patient discomfort.

A commonly used and much less expensive way of screening for colorectal cancer is a fecal occult blood test (FOBT), which tests for the presence of hemoglobin in feces. The presence of hemoglobin in feces is an indicator of intestinal bleeding, which is frequently associated with colorectal cancer. When such fecal blood is detected, a patient can be referred for further medical testing.

FOBT tests fall primarily into two categories, immunochemical tests and tests based on the use of chromogenic chemical reagents such as gum guaiac. Immunochemical tests specifically detect the presence of human hemoglobin in a fecal sample. However, they are more expensive than comparable chemical tests and require more time to obtain a result. In addition, human hemoglobin in fecal samples degrades with time, resulting in a loss of antigenicity which can produce false negative results.

Chemical FOBT tests are, on the other hand, faster and less expensive. The reagents used in such tests, however, sometimes react with animal blood or other substances in fecal samples, producing false positive results at a rate estimated to be in the range of 2%-5%. In order to rule out the possibility of a false positive test result when a chemical FOBT is used, an immunoassay can be performed (see, e.g., U.S. Pat. No. 5,747,344). However, such follow-up immunochemical testing is performed with a different sample of a patient's feces. Since blood may not be present uniformly throughout a fecal specimen or sample, a false negative result is possible, potentially resulting in a patient's cancer going undetected.

SUMMARY

The present system and methods combine the economy and convenience of chemical testing for occult fecal hemoglobin with the specificity and certainty of immunochemical testing. In the present method of testing a fecal sample for the presence of hemoglobin, the sample is first provided on a piece of carrier material, and the sample is contacted with one or more reagents capable of chemically reacting with hemoglobin to produce an indicator of the presence of hemoglobin in the sample. The indicator is preferably a visible indicator such as a stable color signal or a luminescent signal. Chemical reagents capable of producing such a visible indicator include, for example, guaiaconic acid (present in gum guaiac), phenolphthalein, benzidine, 3,3',5, 5'-tetramethylbenzidine, o-tolidine, and luminol. Such chemical reagents typically require the presence of an oxidizer such as hydrogen peroxide, an alkali metal perborate, or potassium monopersulfate (such as OXONE potassium monopersulfate) to produce a visible signal. If an indicator of the presence of hemoglobin in the sample is detected in an indicator area of the carrier material, the portion of the sample present in the indicator area can then be contacted with a specific binding partner for hemoglobin, such as a specific antibody, capable of indicating the presence of human hemoglobin in the sample, in order to confirm that the sample contains hemoglobin. In one embodiment, the indicator area of the carrier material carries at least one chemical reagent, and the sample is placed in contact with such a reagent by applying the sample to the carrier material. Alternatively, the sample can be contacted with the carrier material prior to adding any chemical reagents to it. In this case, such reagents are typically present in solution. Preferably, the carrier material is an absorbent material.

When conducting the immunochemical test portion of the present methods, the indicator area of the carrier material is preferably placed in liquid communication with reagents that specifically bind hemoglobin present on a piece of chromatographic material. Such reagents can comprise monoclonal or polyclonal antibodies or a combination thereof and can be labeled, for example, with colored particles, magnetic particles, metal sols, fluorescent moieties, or luminescent moieties.

To perform the present methods, a system comprising a fecal sample chemical test device and an immunochemical test device can be used. The chemical test device comprises carrier material attached to a handle that further includes a chemical reagent capable of chemically reacting with hemoglobin to produce an indicator of the presence of hemoglobin in the sample. The immunochemical test device includes a receptacle adapted to cooperate with the handle of the chemical test device to place the carrier material of the chemical test device in liquid communication with a piece of chromatographic material attached to the immunochemical test device.

The carrier material of the chemical test device is preferably an absorbent material. The chemical test device further preferably comprises a water-resistant barrier between the handle and the carrier material in order to prevent contact between a sample and an individual performing a test with the present system. The handle is also preferably made from a water-resistant material. In one embodiment, the chemical test device can include two pieces of absorbent material attached to the handle, for testing two samples from a fecal specimen, in which case the handle of the chemical test device and the receptacle of the immunochemical test device are bilaterally symmetrical. The chemical test device can also comprise a cover.

DRAWINGS

These and other features, aspects and advantages of the present invention will become better understood with regard to the following description, appended claims, and accompanying figures where:

FIG. 3 is a top plan view of a blank for forming the test card of FIG. 2.

FIG. 4 is a top plan view of the rear face of the test card of FIG. 2 with the rear flap open.

FIG. 5 is a top plan view of the inner face of an immunochemical test device for use with the chemical test device of FIG. 1.

Figure 1:
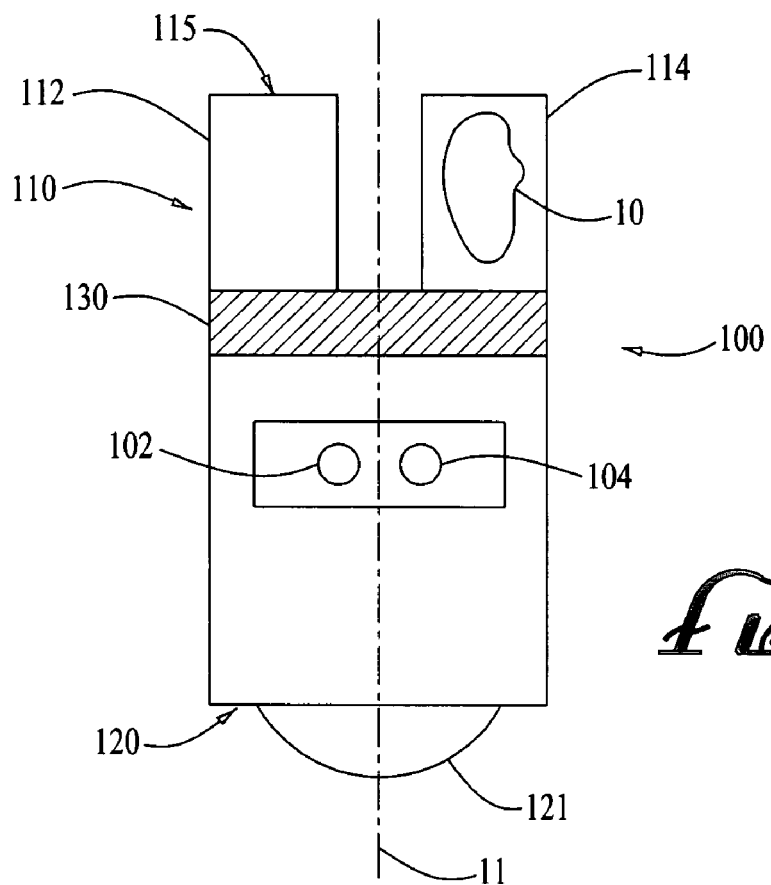
FIG. 1 is a top plan view of the upper surface of an embodiment of a chemical test device for use in the present system.

All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by their intended use.

DESCRIPTION

In order to determine whether a positive result from a chemical FOBT was a false positive result, prior methods required that a different sample of a patient's feces be tested, for example by an immunochemical test, or otherwise that the patient undergo more invasive colonoscopy or sigmoidoscopy procedures. This is because a fecal sample subjected to a chemical FOBT is treated with oxidizing chemicals such as hydrogen peroxide, and it is known that the sensitivity of immunochemical FOBT's can be adversely affected by exposure of samples to some chemicals, such as the sanitizers and detergents in toilet bowls (see, e.g., Imafuku, et al., "The effect of toilet sanitizers and detergents on immunological occult blood tests," Clin. Chim. Acta, 253:51-9 (1996)). Exposing a fecal sample to oxidizing agents such as hydrogen peroxide would thus be expected to degrade hemoglobin and interfere with its detection in an immunochemical FOBT. Another chemical previously thought to interfere with the immunochemical detection of hemoglobin is guaiac (see, e.g., U.S. Pat. No. 4,789,629).

It has unexpectedly been found, however, that a fecal sample subjected to a chemical FOBT can be successfully tested with a subsequent immunochemical FOBT. The present system and methods therefore greatly reduce the need for an endoscopic examination following a positive test result from a chemical FOBT, thereby reducing healthcare costs and the need for a patient to undergo the discomfort of an unnecessary endoscopic examination.

Definitions

"Absorbent material" refers to a material that takes up a liquid on contact.

"Antibody" refers to an antibody, antibody fragment, or antibody derivative which specifically binds to an analyte of interest in an immunochemical FOBT, i.e. to human hemoglobin or a fragment thereof. Such antibodies, fragments and derivatives can be polyclonal, monoclonal, recombinantly produced, or made in other ways known to the art.

"Chemical FOBT" refers to a test to detect the presence of hemoglobin in a fecal sample in which one or more reagents used in the test undergoes a chemical reaction in order to produce an indicator of the presence of hemoglobin in the sample.

"Chromogenic reagent" refers to a color-generating chemical or moiety.

"Epitope" refers to a localized region or regions on the surface of a molecule to which an antibody or other specific binding partner binds.

"Fecal specimen" refers to feces discharged from the bowels of a subject, generally a human subject, during a bowel movement.

"Fecal sample" refers to a portion of feces removed from a fecal specimen.

"Hemoglobin" refers to hemoglobin or fragments thereof, and specifically refers to human hemoglobin unless otherwise indicated.

"Immunochemical FOBT" refers to a test to detect the presence of hemoglobin in a fecal sample in which a specific binding partner, usually an antibody, binds to hemoglobin in order to detect the presence of hemoglobin in the sample.

"Indicator" refers to an indicator of the presence of hemoglobin in a sample. Indicators typically produce visible signals, such as a stable color signal or a luminescent signal.

"Indicator area" refers to the portion of a chemical FOBT in which an indicator is detected.

"Liquid communication" refers to the ability of a liquid used in the present system or methods (such as a liquid carrying the components of a fecal sample and/or a reagent), to pass from one element of the system to a second element, such as from a piece of absorbent material to a piece of chromatographic material. Such communication can result from direct physical contact between the two elements or can alternatively involve an intervening element. Elements of the present system can be said to be in liquid communication in the absence of a liquid, as long as such elements cooperate in such a way that when a liquid is present it is able to flow from one element to the other.

"Specific binding" or "specifically bind," with respect to the interaction between a molecule and a specific binding partner, refers to the attachment of the specific binding partner to the molecule and not to other components of a mixture.

"Specific binding partner" refers to a molecule capable of specifically binding another molecule. A specific binding partner can be any of a number of different types of molecules, including an antibody or other protein, peptide, or polynucleotide (e.g., an aptamer).

"Water-resistant" refers to a material which hinders the penetration or absorption of water.

Reagents

Chemical FOBT Reagents

A number of different chemical reagents known to the art can be used in connection with the chemical FOBT's of the present system and methods. Chemical FOBT's normally involve the use of a chromogenic reagent and an oxidizer which react in the presence of hemoglobin to produce a visible indicator of the presence of hemoglobin in a sample. Oxidizing agents such as hydrogen peroxide are preferably used in concentrations of between about 0.1% and about 10%, more preferably between about 3% and about 6%, and even more preferably between about 4% and about 5%.

A commonly used reagent in chemical FOBT's is gum guaiac, which can be derived from two related species of evergreen trees, *Guaiacum officinale* and *G. sanctum*. Guaiaconic acid [3,4-dimethyl-2,5-bis(4-hydroxy-3-methoxyphenyl)furan], a colorless phenolic compound, is the active ingredient of gum guaiac. In the presence of hemoglobin and an oxidizing agent such as hydrogen peroxide, guaiaconic acid produces a stable blue color signal. When gum guaiac is used in the present system and methods as a chemical reagent, the oxidizing agent used with it is preferably hydrogen peroxide, with solutions of about 4%-5% hydrogen peroxide being preferred. Hydrogen peroxide solutions can include ethanol or methanol, preferably in concentrations of between about 75% and 80%.

In another embodiment of a chemical FOBT, the reagents used can comprise benzidine (4,4'-diaminobiphenyl), which forms a blue precipitate upon oxidation by the heme group of hemoglobin in the presence of hydrogen peroxide or other oxidizing agent. For example, a solution of 0.4% benzidine can be added to a fecal sample followed by the application of a solution of 0.3% hydrogen peroxide in order to produce an indicator of the presence of hemoglobin in the sample.

Several derivatives of benzidine are likewise useful in detecting hemoglobin. One such derivative is 3,3',5,5'-tetramethylbenzidine (TMB), which reacts in the presence of hemoglobin and an oxidizing agent to produce a blue-green color signal. One preferred oxidizing agent for use with TMB is a monopersulfate compound such as potassium peroxymonosulfate ($KHSO_5$, also known as potassium monopersulfate, available as OXONE potassium monopersulfate from DuPont, Wilmington, DE). For example, TMB can be incorporated into an absorbent material together with an organic peroxide compound (such a combination is sold under the trade name EZ DETECT fecal occult blood test kit, available from Biomerica, Inc., Newport Beach, Calif.). Another benzidine derivative which can be used is 3,3'-dimethylbenzidine (o-tolidine).

In another embodiment, the reagents used to detect hemoglobin in a chemical FOBT can comprise phenolphthalein, which produces a pink color upon reaction with hemoglobin in the presence of hydrogen peroxide. The phenolphthalein reagent preferably comprises 80% ethanol, and a solution of 3% hydrogen peroxide is used as the oxidizing agent.

An alternative chemical reagent which can be used in the present system and methods is luminol (5-amino-2,3-dihydro-1,4-phthalazine-dione). Luminol is a chemiluminescent compound. When it is oxidized in the presence of the iron of hemoglobin, such as by a perborate, permanganate, hyperchlorite, iodine, or hydrogen peroxide solution, luminol emits a green-blue light.

Immunoassay Reagents

Immunoassay reagents known to the art can be used in the immunochemical test devices of the present system and methods. Such reagents include antibodies or other specific binding partners which specifically bind to an epitope of the hemoglobin molecule, for example to the globin chain of hemoglobin. While antibodies are typically used as specific binding partners for hemoglobin in an immunochemical FOBT, other specific binding partners can also be used. For example, peptides, aptamers, or other molecules capable of specifically binding hemoglobin can also be used.

A specific binding partner for hemoglobin can be coupled to a detectable label for use in an immunochemical FOBT so that the binding of the specific binding partner to hemoglobin can be detected. The detectable label can be coupled to the specific binding partner by techniques known to the art including, for example, covalent bonding and passive adsorption. The detectable label can be either a direct label, i.e. a label which is directly detectable under the conditions of the assay either through visible inspection or through the use of a detector, or an indirect label. Examples of direct labels include dye sols (e.g., colloidal carbon), metallic sols (e.g., colloidal gold, silver, or iron), fluorescent moieties, radioactive moieties, magnetic particles, and colored latex particles. Indirect labels require the addition of one or more developing reagents, such as substrates or reactants, to facilitate detection. Such labels include luminescent moieties and enzymes such as alkaline phosphatase and horseradish peroxidase, which can be detected when contacted with a chromogenic substrate.

Immunochemical FOBTs are typically sandwich assays, in which the labeled specific binding partner binds to one epitope of hemoglobin and a second specific binding partner attached to a solid support binds either to the first specific binding partner or to a spatially distinct epitope on hemoglobin. Other methods known to the art for detecting hemoglobin with specific binding partners can also be used, however. In addition to specific binding partners, an extraction buffer or other carrying liquid can be combined with a fecal sample in order to place the sample in liquid communication with an immunochemical test device. Extraction buffers preferably comprise an aqueous solution at controlled pH which includes salts, surfactant, preservatives, proteins (such as bovine serum albumin), and phosphate buffered saline.

Devices

Chemical Test Device

The present system includes devices for collecting and chemically testing one or more samples from a fecal specimen. As shown in FIG. 1, the chemical test device 100 comprises a carrier 110 for retaining a fecal sample 10. Since at least some of the chemical reagents used to generate an indicator of the presence of hemoglobin in samples can be administered in solution, the carrier 110 preferably comprises an absorbent material, so that it can retain both the fecal sample 10 and a chemical solution applied to the sample to generate the indicator of the presence of hemoglobin in the sample.

The absorbent material can be, for example, an open-cell, chemically inert matrix, such as porous plastic, filter paper, glass fiber, or a combination of filter paper and glass fiber. Such materials allow rapid desiccation of a sample, minimizing the possibility of sample breakdown due to continued exposure to a liquid environment if the sample is not immediately tested for the presence of hemoglobin. The absorbent material chosen should not react with hemoglobin in a sample or with the reagents necessary to generate an indicator of the presence of hemoglobin, in order to avoid generating false positive or false negative results. In one embodiment, the absorbent material is a cotton cellulose fiber-based filter paper such as Type 950, manufactured by Ahlstrom Filtration, Inc. (Helsinki, Finland).

In a preferred embodiment, the absorbent material is impregnated with a chemical reagent capable of chemically reacting with hemoglobin in a fecal sample to produce an indicator of the presence of hemoglobin in the sample. The chemical reagent can be, for example, gum guaiac. After application of a fecal sample to an absorbent material comprising gum guaiac, a solution comprising hydrogen peroxide can be added to the absorbent material in order to produce a visible indicator if hemoglobin is present in the sample 10.

Preferably, the chemical test device 100 comprises a handle 120 to facilitate the transport of the carrier 110 to an immunochemical test device 200 (see FIGS. 5-9), and preferably to guide the placement of the carrier 110 in the test device 200. As shown in FIG. 1, the handle 120 is disposed at one end of the carrier 110 and provides a gripping portion 121 which is not in contact with the carrier 110. The handle 120 is preferably made from a water resistant material, such as coated SBS, to limit and preferably prevent any liquid flow from the carrier 110 to the handle 120 and thereby prevent contact between a user of the chemical test device 100 and a fecal sample 10 carried on the device 100.

In a further preferred embodiment, a liquid barrier 130 is applied to the carrier 110 between the handle 120 and the sample retaining end 115 of the carrier 110 to further limit liquid (such as an extraction buffer) from wicking into the handle 120 from the carrier 110. The liquid barrier 130, which preferably extends along the entire area comprising the boundary between the carrier 110 and the handle 120, can be formed from any of a number of water-resistant materials, such as wax, starch, or water-insoluble polymers such as polyurethane, polyacrylate and polyvinyl alcohol.

The carrier 110 preferably comprises two sections 112, 114 which are not in liquid communication with each other. The two sections 112, 114 are adapted to retain two different fecal samples from a fecal specimen. This is advantageous because fecal blood may not be uniformly present in a specimen, and testing samples from two different portions of a fecal specimen increases the likelihood of detecting blood in the specimen. In the embodiment shown in FIG. 1, the sections 112, 114 are separated by the liquid barrier 130. It is also preferred that the chemical test device 100 comprise a positive control 102 and a negative control 104, in order to confirm that a test performed with the device 100 is both capable of indicating the presence of hemoglobin (the positive control) and that the lack of any visible indicator produced by the test is not a false negative (the negative control).

Figure 2:
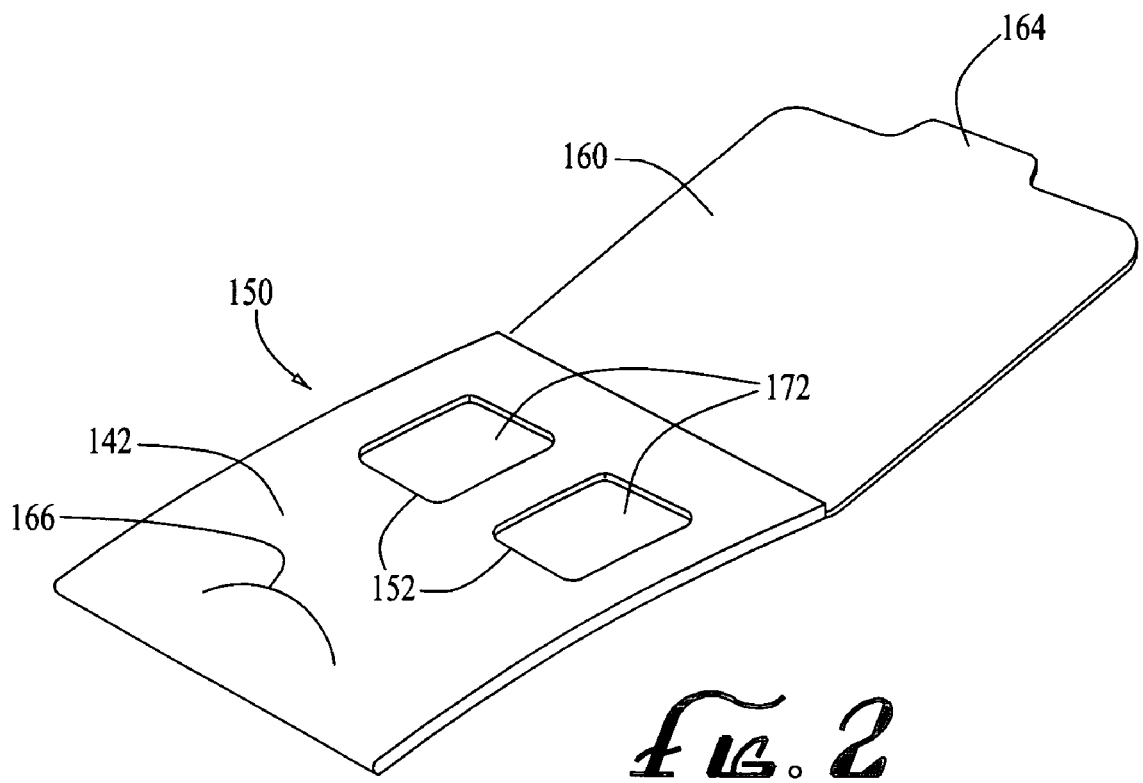
FIG. 2 is a right perspective view of a test card comprising the chemical test device of FIG. 1 with the cover flap open.
Figure 3A:
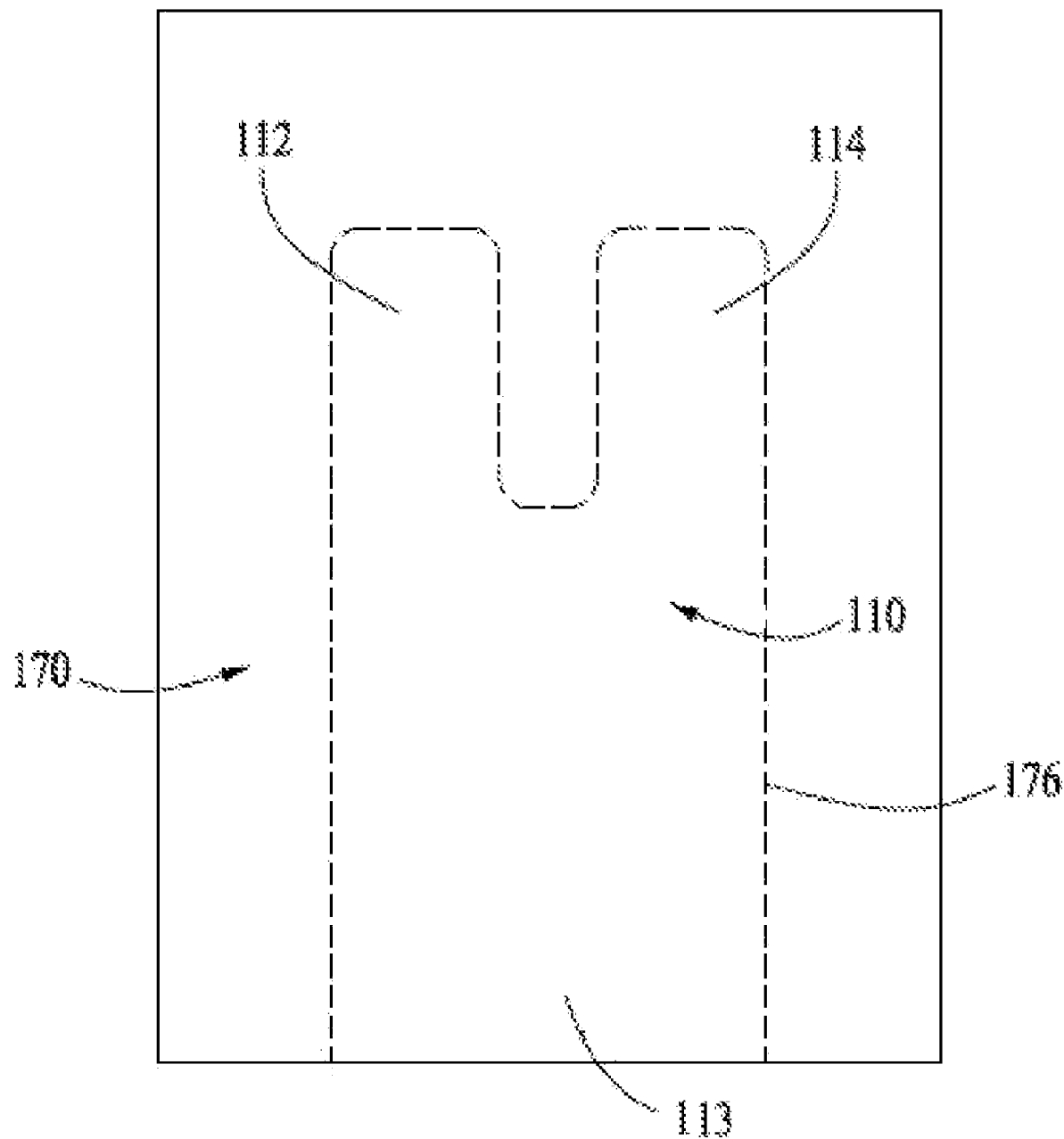
FIG. 3A is a top plan view of a blank for use in forming the test card of FIG. 2.

In one embodiment, shown in FIGS. 2-4, the chemical test device 100 is provided in the form of a test card 150, such as the Hemoccult fecal blood test (available from Beckman Coulter, Inc., Fullerton, Calif.). As shown in FIG. 2, the card 150 preferably comprises a cover 160 which is opened (as shown in FIG. 2) prior to use. The test card 150 can be die cut from a blank 140 as shown in FIG. 3. The blank 140 includes a front face 142 and a rear face 144, which comprise outer surfaces of the test card 150 following assembly. The front face 142 and rear face 144 are folded along fold line 143, as shown in FIG. 3, in order to assemble the test card 150. A blank 170 (shown in FIG. 3A) comprising an absorbent material is die cut to form the carrier 110 and is attached, such as by gluing, to the inner surfaces of one or both of the front face 142 and the rear face 143 such that the sections 112, 114 of the carrier 110 line up with windows 152. A portion of the inner surfaces (not shown) of the front face 142 and rear face 144 are secured to each other, such as via the blank 170 which is sandwiched between them, in order to form the test card 150 as shown in FIG. 2. To finish the assembly, the cover 160 is folded along fold line 162 in order to cover the front face 142, and tab 164 can be inserted into slot 166 in order to secure the cover 160 to the test card 150.

It is important, however, that rear flap 180 not be attached to either the front face 142 or to the blank 170 between the handle 120 and (after folding) the windows 152, so that it can be lifted open, i.e. by separating it along separation line 182 and folding it along fold line 184. In this way, when one or more fecal samples are applied to the upper surface 172 of the sections 112, 114 of the carrier 110, chemical reagents can be applied to the lower surface 174 by lifting the rear flap 180. In addition, the handle 120 should be attached, such as by gluing, to the lower portion 113 of the carrier 110. In this way, when a positive chemical FOBT is detected in one or both of the sections 112, 114 of the carrier 110, the carrier 110 and handle 120 can be removed from the test card 150 by separating the handle 120 from the test card along separation line 124 (the handle already having been separated from the rear flap 180 along separation line 126) and lifting the handle 120 so as to separate the carrier 110 from the blank 170 along separation line 176.

In another embodiment (not shown), the carrier 110 is provided in the form of a plurality of separate or separable strips or pieces of carrier material, each of which preferably includes a handle. In this embodiment, a plurality of chemical tests can be performed, and only those carriers 110 in which a positive test result is found are then subjected to immunochemical testing according to the present methods. In this embodiment, as in other embodiments, the carrier 110 can be attached to a handle 120, and can be incorporated into a test device such as a test card 150.

Immunochemical Test Device

Figure 6:
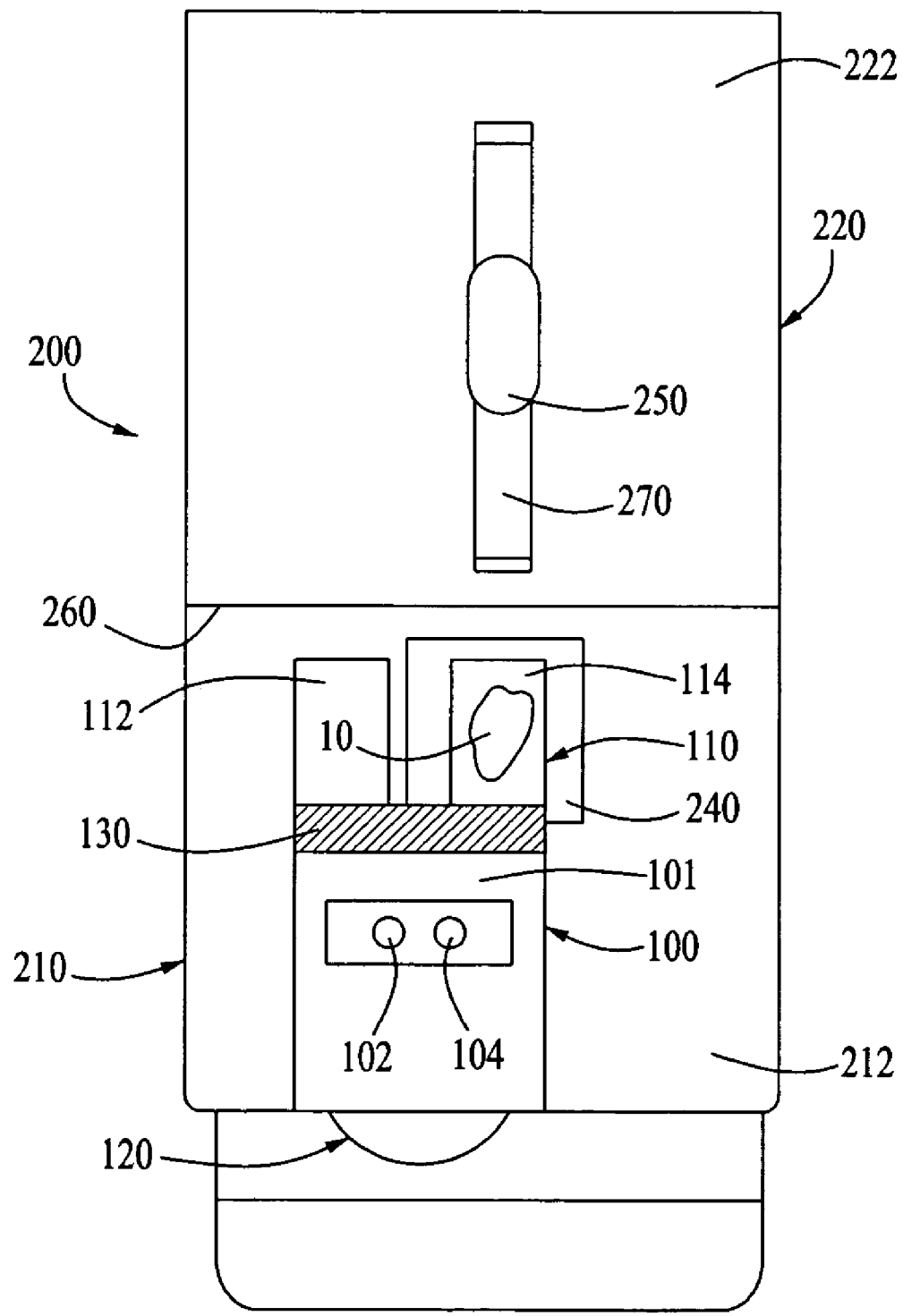
FIG. 6 is a top plan view of the inner face of the immunochemical test device of FIG. 5 with the chemical test device of FIG. 1 positioned for performing an immunoassay.

The present system further includes immunochemical test devices 200 for confirming the results of a chemical FOBT. As shown in FIG. 5, the immunochemical test device 200 of the present system preferably comprises a receptacle 230 that is shaped to accept the handle 120 of the chemical test device 100. The receptacle 230 is positioned in the test device 200 so as to facilitate the proper placement of the carrier 110 of a chemical test device 100 in the immunochemical test device 200, i.e. such that the carrier 110 is placed in liquid communication with chromatographic material used in performing an immunochemical FOBT with the device 200, as shown in FIG. 6. The receptacle 230 can facilitate liquid communication with chromatographic material 250 on the device 200 directly or via an absorbent material 240 on the test device 200.

In the embodiment shown in FIGS. 5-9, the test device 200 comprises a base member 210 and a cover member 220 having opposed inner surfaces 212 and 222. The base member 210 and cover member 220 are preferably formed from a single piece of material, such as coated SBS, and are preferably hingedly connected, such as along fold line 260. Such a test device 200 is available, for example, from Beckman Coulter, Inc., Fullerton, Calif. as Hemoccult ICT.

The base member 210 of the test device 200 in this embodiment includes the receptacle 230 and a sample pad 240 for receiving analytes from the carrier 110 of the chemical test device 100. The sample pad 240 is preferably constructed from several layers of material. The uppermost layer of the sample pad 240, which is in direct or at least in liquid communication with the carrier 110 when carrier 110 is positioned in the receptacle 230, comprises an absorbent sample pad material which is inert, i.e. it does not bind (or does not significantly bind) or react with hemoglobin. The absorbent sample pad material can be made of any absorbent material that will hold liquid sufficiently so that liquid from a fecal sample (typically a reconstituted sample), including buffers or other assay reagents, can be accumulated in the absorbent sample pad material and then drawn through the chromatographic material 250 when it is placed in communication with the chromatographic material 250. Typical materials for the sample pad material include, but are not limited to, glass fiber, porous plastic, cellulose, filter paper, and combinations of glass fiber and cellulose. The size and shape of the sample pad 240 can be chosen according to the volume of fluid used in the immunochemical FOBT.

In this embodiment, a layer of foam or cushioning material is preferably present below the absorbent sample pad material. When the cover member is closed over the test device 200 and a conjugate pad 270 contacts the carrier 110, the conjugate pad 270 preferably slightly compresses the cushioning material of the sample pad 240, which causes the cushioning material to exert pressure back on the carrier 110.

This serves to maintain the carrier 110 of the chemical test device 100 in liquid communication with the conjugate pad 270. Preferably, the conjugate pad 270 of the test device and the carrier 110 of the chemical test device 100 are placed in physical contact in order to assure that any hemoglobin is able to pass from the carrier 110 into the conjugate pad 270 and then on to the chromatographic material 250. A piece of structurally stronger material, such as LEXAN polycarbonate (available from GE Structured Products, Pittsfield, Mass.), can be bonded to the underside of the cushioning material to allow it to be attached to the immunochemical test device 200 during manufacturing.

The cover member 220 of the test device 200 in the embodiment of FIGS. 5-9 includes a piece of chromatographic material 250 used to detect the presence of hemoglobin in a sample. Preferably, the conjugate pad 270 comprises a labeled specific binding partner for hemoglobin, such as labeled antibodies, while the chromatographic material 250 comprises an immobilized specific binding partner for hemoglobin. The immobilized specific binding partner binds hemoglobin and thereby immobilizes it on the chromatographic material. The immobilized hemoglobin can then be detected, e.g., by detecting a labeled specific binding partner bound to the hemoglobin molecule in the chromatographic material 250.

The chromatographic material 250 can be any suitable material, such as nitrocellulose, filter paper, or a membrane made from a polymer material such as nylon. One suitable polymer material is the LATERAL FLO membrane, a polyethylene material sold by Porex Corporation (Fairburn, Ga.). Preferably, the chromatographic material 250 has a pore size of at least about 1 micron and more preferably of about 5-20 microns. The cover member 220 of the test device 200 can further include a conjugate ribbon (not shown), which can be made from a non-woven material such as polyester, in communication with the conjugate pad 270 in order to smooth the transfer of liquid from the carrier 110 into the conjugate pad 270.

Figure 7:
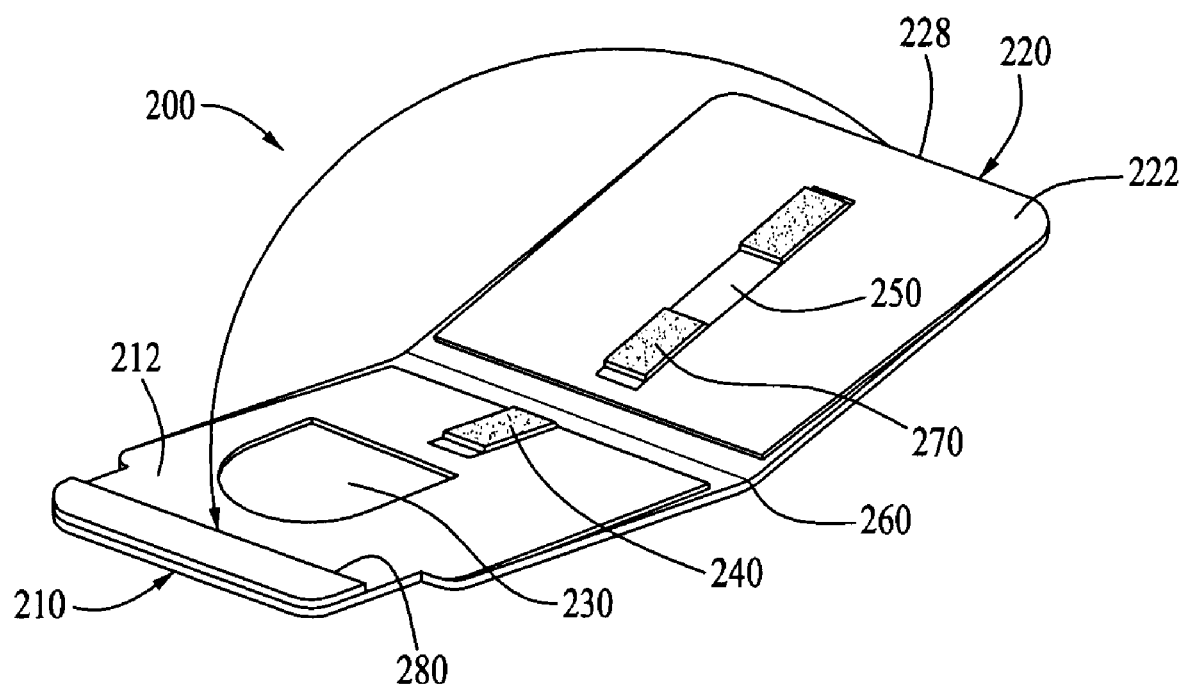
FIG. 7 is a right side perspective view of the immunochemical test device of FIG. 5 illustrating how the device is closed when performing an immunoassay.
Figure 8:
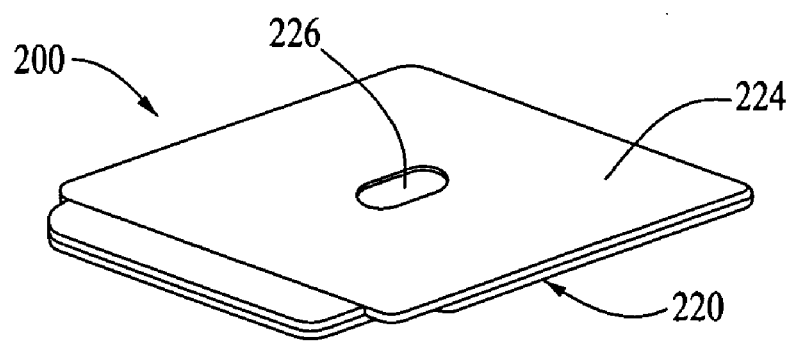
FIG. 8 is a right side perspective view of the immunochemical test device of FIG. 5 in a closed position.

In order to place the sample pad 240 and the carrier 110 in liquid communication with the conjugate pad 270 and chromatographic material 250 in this embodiment, the interior surface 222 of the cover member 220 is moved toward the interior surface 212 of base member 210 by bending the cover member 220 along fold line 260, as shown in FIG. 7. The test device 200 is thereby closed. When it is in the closed position, as shown in FIG. 8, conjugate pad 270 is placed in liquid communication with the sample pad 240, thereby allowing liquid in the carrier 110 and in the sample pad 240 on the base member 210 to flow into the conjugate pad 270 on the cover member 220 and then into the chromatographic material 250. The test device 200 can be maintained in a closed position, for example, by a beveled surface 280 on the base member 210 which cooperates with the outer edge 228 of the cover member 220.

Figure 9:
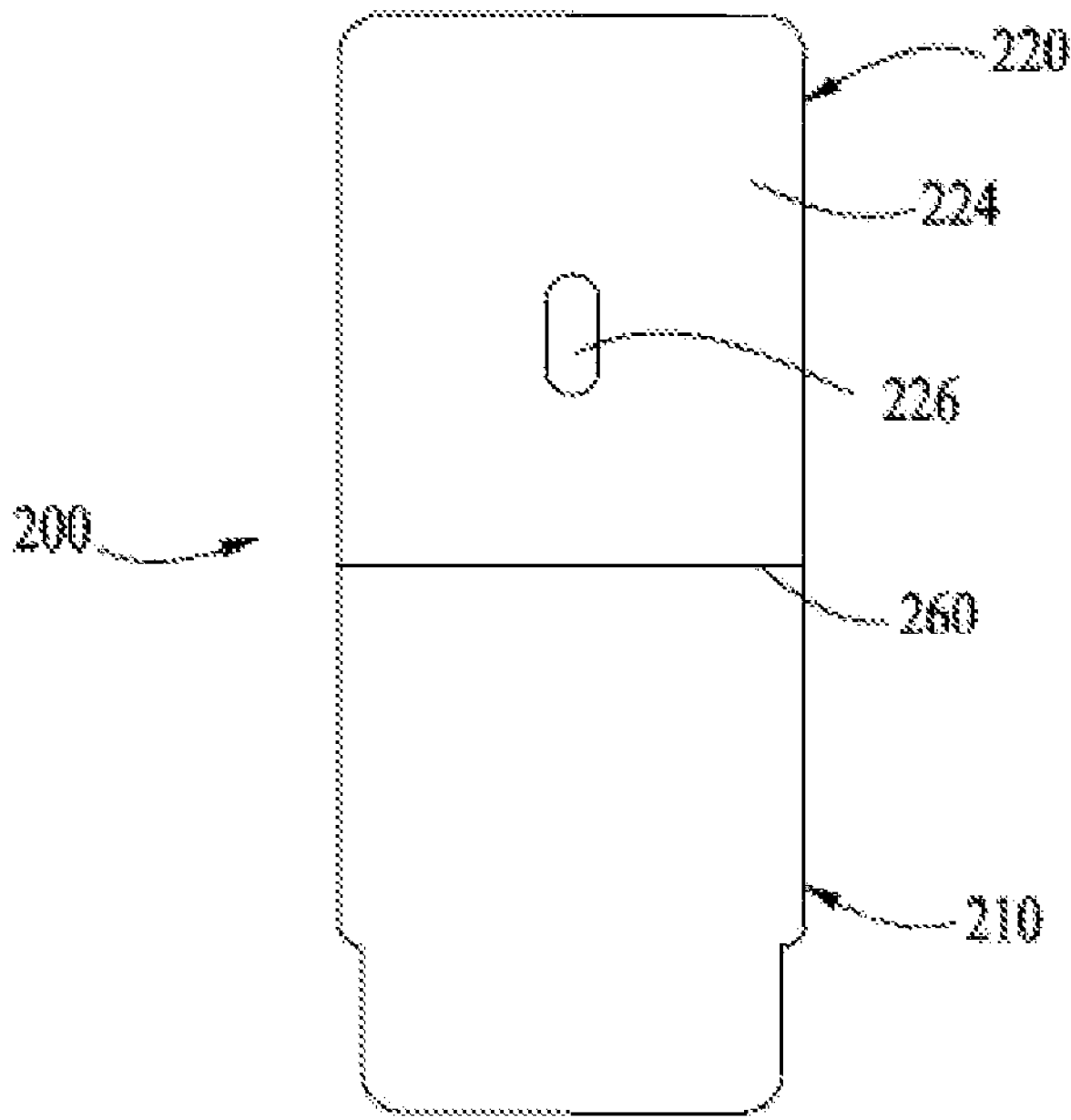
FIG. 9 is a top plan view of the outer face of the immunochemical test device of FIG. 5.

As shown in FIGS. 8 and 9, the chromatographic material 250 in this embodiment preferably overlies an opening or window 226 in the cover member 220, such that the assay results obtained from performing a test with the chromatographic material 250 can be visualized through the window 226 in the cover member 220. In this embodiment, the piece of the chromatographic material 250 is attached to the interior surface 222 of the cover member 220, and preferably extends across the window 226. At least a portion of the chromatographic material 250 is visible from the window 226, i.e. it is within or beneath the window, and this portion includes the immobilized specific binding partner, i.e. the detection area of the chromatographic material 250. The window 226 can include a sheet of transparent material such as LEXAN polycarbonate interposed between the chromatographic material 250 and the exterior side 224 of the cover member 220.

In a preferred embodiment, shown in FIG. 1, the carrier 110 comprises two sections 112, 114 of absorbent material. Since a sample in either section might comprise hemoglobin, the chemical test device 100 and immunochemical test device 200 are preferably configured so that either section of the carrier 110 can be placed in communication with the absorbent material 240 and ultimately with the chromatographic material 250 of the test device 200. In the embodiment shown in FIG. 6, the handle 120 and receptacle 230 are bilaterally symmetrical with respect to an axis of symmetry 11 (shown in FIG. 1) running from the carrier end of the handle 120 to the gripping portion 121 (and with respect to the corresponding portion of the receptacle 230), such that handle 120 will fit into the receptacle 230 either when upper face 101 of the chemical test device 100 faces away from interior surface 212 of the base member 210 or when upper face 101 faces toward interior surface 212. In this way, either section 112, 114 can be tested to confirm the presence of hemoglobin in a sample.

Methods

Collecting a Sample

In order to perform a FOBT according to the present methods, a specimen of feces is first obtained. A fecal specimen can be collected in ways known to the art, such as by depositing a specimen on a piece of plastic or paper placed over the water in a toilet bowl. It is important to keep the specimen from contacting the water in a toilet bowl to the extent possible, since blood may only be present on the surface of a specimen and might be washed away from the specimen should it come into contact with water, which could lead to a false negative test result.

Once a specimen is obtained, a sample from the specimen is collected. Using a flattened stick or other applicator, a pea-sized sample can be removed and placed on one of the sections of absorbent material 112, 114 of the carrier 110 and spread across it. A second pea-sized sample is next preferably collected from a second area of the specimen and applied to the other section of absorbent material (112 or 114). In the embodiment shown in FIGS. 2-4, the cover 160 of the test card is first opened in order to allow a sample to be applied to the absorbent material 170.

Alternatively, fecal samples can be collected as disclosed in U.S. Pat. No. 6,869,804. Fecal material can be contacted with a fluid such as water, and a sample of the fluid can subsequently be collected using a brush or a brush-like device having flexible or semi-flexible elongate strands, laminar flaps or the like. A small artist's paint brush having bristles about 1 to 2 cm in length, for example, can be used for sampling. The brush can be used to "paint" the surface of the fecal material so as to displace any blood on the surface into the water or other fluid surrounding the material. A sample is then collected from the fluid within the bristles of the brush. The flexible or semi-flexible bristles of the brush will be relatively "open" during this brushing and sampling process, but will "close" as the brush is withdrawn from the water, thereby keeping a sample of the water (and any blood contained therein), within the interstitial spaces of the bristles. This sample can then be transferred to a suitable assay device for subsequent testing. This method of obtaining a fecal sample can be advantageously used with a chemical FOBT when one or more reagents to be reacted with hemoglobin in a chemical FOBT are in liquid form, such as when guaiaconic acid is used in a chemical FOBT.

Performing a Chemical Test

To perform a chemical FOBT, the appropriate chemical reagents can be applied to a fecal sample carried on the carrier 110. If the carrier 110 comprises gum guaiac, for example, an alcohol-based solution comprising 4%-5% hydrogen peroxide is applied to the sections 112, 114 of absorbent material 170 carrying the sample in order to produce an indicator of the presence of hemoglobin in the sample. Alternatively, the sample can be applied to a carrier 110 which does not contain a chemical reagent, and one or more solutions comprising an appropriate chemical reagent or reagents can be applied to the sample on the carrier 110. The sections 112, 114 of absorbent material 170 which carry the sample and are treated with chemical reagents comprise the indicator area of the chemical test device 100, as any indicator of the presence of hemoglobin in the sample will be detectable in this area.

In a further alternative, a fecal sample can be reacted with one or more chemical reagents in solution and then be applied to a carrier material. For example, a solution comprising guaiaconic acid can be contacted with a fecal sample, and the resulting chemically reacted mixture can be applied to a solid support, such as a carrier 110. The indicator of the presence of hemoglobin can be developed in this case by contacting the resulting solution on the carrier with an oxidizing agent such as hydrogen peroxide. If desired, the indicator can be developed entirely in solution and then applied to a carrier, or can be applied directly to an immunochemical FOBT.

Performing an Immunoassay

After performing a chemical test on a fecal sample, if the test results indicate that hemoglobin is present in the sample, those results can then be confirmed according to the present methods by performing a confirmatory immunochemical test. Such an immunochemical test is performed by testing at least a portion of the chemically reacted a sample in which an indicator of the presence of hemoglobin has been detected in a chemical FOBT with an immunochemical FOBT. Such a sample portion has been exposed to the chemical reagents used in the chemical FOBT and includes or expresses the indicator. Generally, the chemically reacted portion of a sample containing the indicator is present on a carrier 110 of a chemical test device.

A chemically reacted sample on the carrier 110 is preferably placed in direct contact with a chromatographic material of an immunochemical FOBT or with an absorbent material in liquid communication with such chromatographic material, so that sample components (hemoglobin, in particular) are placed in liquid communication with specific binding partners for hemoglobin in and/or on such chromatographic material. As shown in FIG. 6, the sample is preferably carried on a chemical test device 100 which comprises a handle 120, and the immunochemical test comprises a receptacle 230 which cooperates with the handle 120 so that when the handle 120 is placed in the receptacle 230, the carrier 110 in which an indicator of the presence of hemoglobin has been detected is in liquid communication with a piece of chromatographic material 250 on which an immunoassay can be performed.

The chemically reacted sample is generally treated, such as with an extraction buffer, in order extract it from the carrier 110 of the chemical test device 100 and carry out an immunochemical FOBT. When the embodiment of the test device 200 shown in FIGS. 5-9 is used to perform an immunochemical FOBT, the cover member 220 is then closed, and a chromatographic material 250 is thereby placed in communication with the sample in the carrier 110. The extracted sample flows from the carrier 110 (and from the sample pad, if any sample has migrated into the sample pad 240 after the application of an extraction buffer) into the conjugate pad 270. The assay results are then read through window 226 after an appropriate amount of time, to determine whether a specific binding partner for hemoglobin in the chromatographic material has bound hemoglobin present in the sample, such as by detecting the label of another specific binding partner that has bound to such hemoglobin.

Use of Assay Results

The results of a confirmatory immunochemical FOBT on a sample following a chemical FOBT indicating the presence of hemoglobin can be used to determine an appropriate course of further medical testing and/or treatment for a patient. Medical conditions associated with the presence of blood in feces which can be monitored and/or treated according to the present methods include iron deficiency anemia, recovery from surgery, peptic ulcer, ulcerative colitis, and colorectal cancer.

The present methods can in particular be used to determine what further diagnostic tests are indicated for a patient. A positive result of a chemical FOBT generally reflects the presence of blood somewhere in the gastrointestinal tract. A negative confirmatory immunochemical FOBT test result can, in some instances, indicate that a patient may have bleeding in the upper gastrointestinal (GI) tract, since the hemoglobin molecule is not believed to survive intact during its transit from the upper GI tract to the lower GI tract, though heme (which is tested for by most chemical FOBT tests) does survive. Bleeding from the lower GI tract, on the other hand, is less likely to result in the degradation of the whole hemoglobin molecule, so that a positive immunochemical FOBT is likely to be indicative of bleeding in the lower GI tract. Such localization of patient bleeding is an important benefit of the present methods, since it allows a clinician to choose an appropriate further diagnostic test, e.g. an endoscopic examination of either the stomach or of the large bowel, thereby reducing the number of unnecessary procedures that a patient might otherwise undergo.

Kits

The chemical test devices 100 and immunochemical test devices 200 can advantageously be provided together as kits. Preferably, the chemical test devices 100 provided in such kits are capable of testing six different samples, i.e. two samples from each of three fecal specimens collected on three consecutive days, in order to provide an accurate assessment of a patient's condition. For home use, a single test device 200 can be provided with one or more chemical test devices 100 capable of testing an appropriate number of fecal samples (e.g., six samples). In another embodiment, when a number of different patients are being screened for fecal blood, such as in a hospital, a larger number of chemical test devices 100 are provided for each test device 200 provided. The number of chemical test devices 100 provided for each test device 200 would correspond to the number of expected positive results when a given number of chemical FOBT's are performed with the chemical test devices 100.

EXAMPLES

Example 1

Detection of Occult Fecal Hemoglobin

Microliter quantities of human blood collected by fingerstick were smeared onto all six windows of a Hemoccult slide comprising gum guaiac. After overnight drying, developer solution (comprising between 4% and 5% hydrogen peroxide) was added. This resulted in blue color in all windows, i.e. a positive test for blood. The slide was allowed to dry overnight to maximize the exposure of the blood to the developer solution.

The next day, samples of the blue filter paper were removed using a quarter inch diameter paper punch. Each disc was placed onto the sample pad of a Hemoccult ICT test device, which is an immunochemical FOBT comprising polyclonal antibodies directed against human hemoglobin. Extraction buffer provided with the test device was added to each disc, and an immunochemical test was allowed to proceed for five minutes (pursuant to instructions provided with the Hemoccult ICT test). At the end of that period, all of the devices showed a positive result for hemoglobin.

Example 2

Effect of Developer Solution on the Detection of Occult Fecal Hemoglobin

An experiment was conducted as in Example 1, except that the positive-testing guaiac slides were tested with a Hemoccult ICT test immediately after the developer solution was added and also 15 minutes after the addition of developer solution. In both cases, the Hemoccult ICT test produced a positive result for the presence of human hemoglobin.

Example 3

Use of Positive Immunochemical Test Results

A technician tests a sample of a patient's feces with a Hemoccult slide and with a Hemoccult ICT test as described in Example 1. Both the chemical (Hemoccult) test and immunochemical (Hemoccult ICT) test produce positive results for the presence of human hemoglobin in the fecal sample. A physician reviews these results and orders a visual examination of the lower gastrointestinal tract of the patient.

Example 4

Use of Negative Immunochemical Test Results

A technician tests a sample of a patient's feces with a Hemoccult slide and with a Hemoccult ICT test as described in Example 1. The chemical (Hemoccult) test produces positive results for the presence of hemoglobin in the fecal sample, but the immunochemical (Hemoccult ICT) test produces negative results. A physician reviews these results and further examines and/or tests the patient for signs or symptoms of upper gastrointestinal bleeding (or orders that such examination and testing be performed by another). Such testing can include a visual examination of the upper gastrointestinal tract of the patient. In case no upper gastrointestinal bleeding is detected, a physician instructs that the patient be re-tested for the presence of human hemoglobin after an appropriate period of time, such as one year, in order to confirm that the patient in fact is not experiencing gastrointestinal bleeding.

Although the present invention has been discussed in considerable detail with reference to certain preferred embodiments, other embodiments are possible. Therefore, the scope of the appended claims should not be limited to the description of preferred embodiments contained in this disclosure. All references cited herein are incorporated by reference to their entirety.

What is claimed is:

1. A method of determining whether hemoglobin is present in a fecal sample, comprising the steps of:
   (a) applying the sample to an absorbent matrix material:
   (b) contacting the sample with one or more chemical reagents capable of chemically reacting with hemoglobin in the sample, wherein the one or more chemical reagents comprise guaiaconic acid;
   (c) contacting the sample and the guaiaconic acid in the absorbent matrix material with an oxidizing agent, thereby producing an indicator of the presence of hemoglobin in the sample;
   (d) detecting the indicator in the absorbent matrix material;
   (e) after step (d), placing a portion of the sample in which the indicator is detected in liquid communication with a first specific binding partner for hemoglobin, wherein the first specific binding partner is present in a chromatographic material; and
   (f) detecting binding of the first specific binding partner to hemoglobin in the chromatographic material in order to determine whether hemoglobin is present in the sample.

2. The method of claim 1, wherein the sample is applied to the absorbent matrix material prior to performing step (b).

3. The method of claim 2, wherein step (d) comprises detecting the indicator in an indicator area of the absorbent matrix material.

4. The method of claim 3, wherein the indicator area of the absorbent matrix material carries at least one of the one or more chemical reagents prior to being contacted with the sample, and wherein step (b) occurs when the sample is applied to the absorbent matrix material.

5. The method of claim 4, wherein the indicator area of the absorbent matrix material comprises gum guaiac.

6. The method of claim 3, wherein step (e) comprises placing the indicator area in liquid communication with the first specific binding partner for hemoglobin.

7. The method of claim 1, wherein a second specific binding partner for hemoglobin is secured to a detection area of the chromatographic material.

8. The method of claim 1, wherein the first specific binding partner comprises a polyclonal antibody.

9. The method of claim 8, wherein the polyclonal antibody is conjugated to a label selected from the group consisting of a colored particle, a magnetic particle, a metal sol, a fluorescent moiety, and a luminescent moiety.

10. The method of claim 1, wherein the oxidizing agent is hydrogen peroxide.

11. The method of claim 1, wherein at least one of the one or more chemical reagents is present in solution.

12. The method of claim 1, wherein hemoglobin is determined not to be present in the sample.

13. The method of claim 1, wherein the absorbent matrix material and the chromatographic material are both made from filter paper.

14. The method of claim 1, further comprising the step of desiccating the sample after step (a).

* * * * *